(12) United States Patent
Niederwanger et al.

(10) Patent No.: US 7,223,099 B2
(45) Date of Patent: May 29, 2007

(54) METHOD OF DETERMINING THE SELECTION OF BRACKETS WHICH ARE TO BE USED IN THE ORTHODONTIC TREATMENT OF TEETH MALPOSITION

(76) Inventors: Andreas Niederwanger, Schulgasse 39, A-6162 Mutters (AT); Wolfgang Heiser, Dr.-Stumpf-Strasse 73, A-6020 Innsbruck (AT); Siegfried Kulmer, Medizinzentrum Anichstrasse, Anichstrasse 35, A-6020 Innsbruck (AT)

( * ) Notice: Subject to any disclaimer, the term of this patent is extended or adjusted under 35 U.S.C. 154(b) by 331 days.

(21) Appl. No.: 11/050,977

(22) Filed: Feb. 4, 2005

(65) Prior Publication Data

US 2005/0175955 A1 Aug. 11, 2005

(30) Foreign Application Priority Data

Feb. 6, 2004 (DE) ...................... 10 2004 006 009

(51) Int. Cl.
  *A61C 3/00* (2006.01)
(52) U.S. Cl. ............................................. 433/24; 433/8
(58) Field of Classification Search .................. 433/24, 433/8, 18, 20; 702/150–153; 382/100, 154, 382/286, 291; 348/66
See application file for complete search history.

(56) References Cited

U.S. PATENT DOCUMENTS

| | | | | |
|---|---|---|---|---|
| 3,660,900 | A | | 5/1972 | Andrews |
| 5,368,478 | A | * | 11/1994 | Andreiko et al. ............. 433/24 |
| 5,464,349 | A | * | 11/1995 | Andreiko et al. ............. 433/24 |
| 5,474,448 | A | * | 12/1995 | Andreiko et al. ............. 433/24 |
| 5,533,895 | A | * | 7/1996 | Andreiko et al. ............. 433/24 |
| 5,879,158 | A | * | 3/1999 | Doyle et al. .................. 433/24 |
| 2003/0096209 | A1 | * | 5/2003 | Sugiyama et al. ............. 433/8 |
| 2004/0259049 | A1 | * | 12/2004 | Kopelman et al. ............ 433/24 |
| 2005/0130095 | A1 | * | 6/2005 | Raby et al. ................... 433/24 |
| 2006/0147872 | A1 | * | 7/2006 | Andreiko ...................... 433/24 |

OTHER PUBLICATIONS

Stomatologie 96.3, vol. 3, May 1999, pp. 045-053 "Anatomische und funktionelle Details der Schneidezähne natürlich gewachsener unbehandelter Jugendlicher und Messwerte der Schneidezähne im internationalen Vergleich" (by B. Ruzicka, M. Stainer, A. Niederwanger and S. Kulmer).

Dtsch Zahnärztl Z 54 (1999) 5, pp. 325-328 "Neigung und Sequenz von Führungselementen in gruppengeführten Okklusionen" (by M. Stainer, M. Hilbe, W. Leja and S. Kulmer).

Journal of Oral Rehabilitation 1999, 26, pp. 650-660 "Incline and length of guiding elements in untreated naturally grown dentition" (by S. Kulmer, B. Ruzicka, A Niederwanger and I. Moschen).

* cited by examiner

*Primary Examiner*—Ralph A. Lewis
*Assistant Examiner*—Sunil K. Singh
(74) *Attorney, Agent, or Firm*—Jansson Shupe & Munger Ltd.

(57) ABSTRACT

To determine the required torque angle of a bracket for the orthodontic treatment of teeth malposition the angle between the bracket plane and the axis-orbital plane is determined, for the respective tooth a guiding straight line or guiding plane is determined, the anatomy of the tooth on its front side is measured, and the torque angle of the bracket to be used is calculated in consideration of a predetermined angle of intersection between the guiding straight line or guide plane and the axis-orbital plane.

12 Claims, 6 Drawing Sheets

FIG. 2
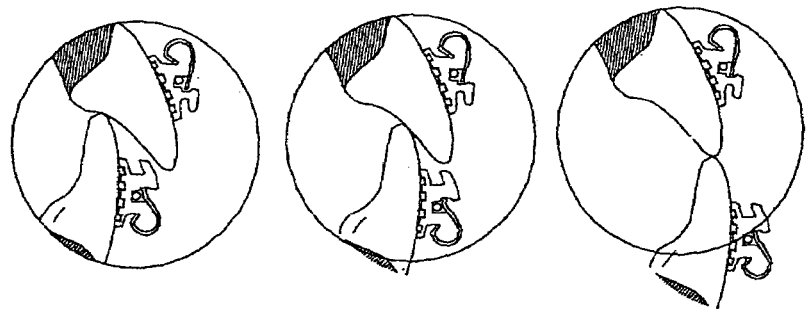
(c) (b) (a)
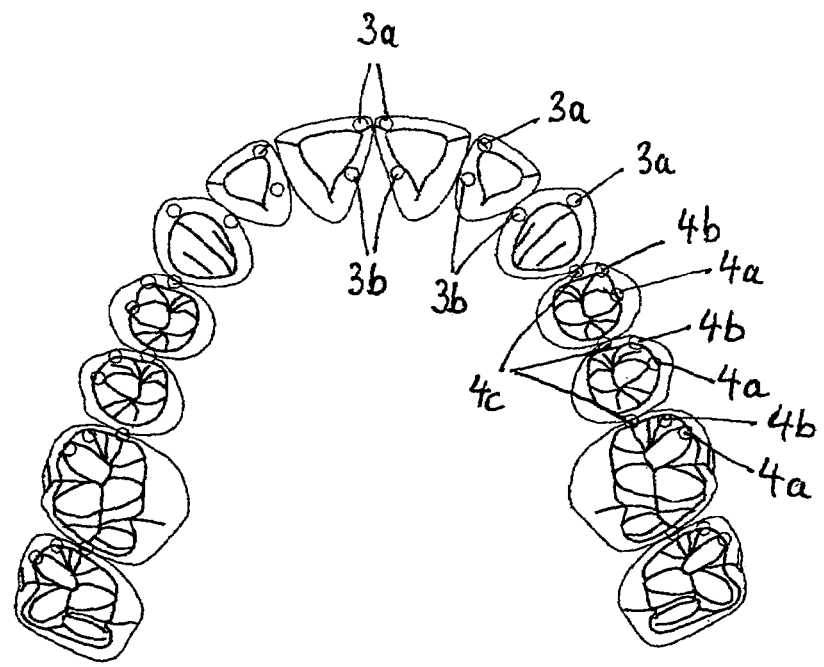
FIG. 3

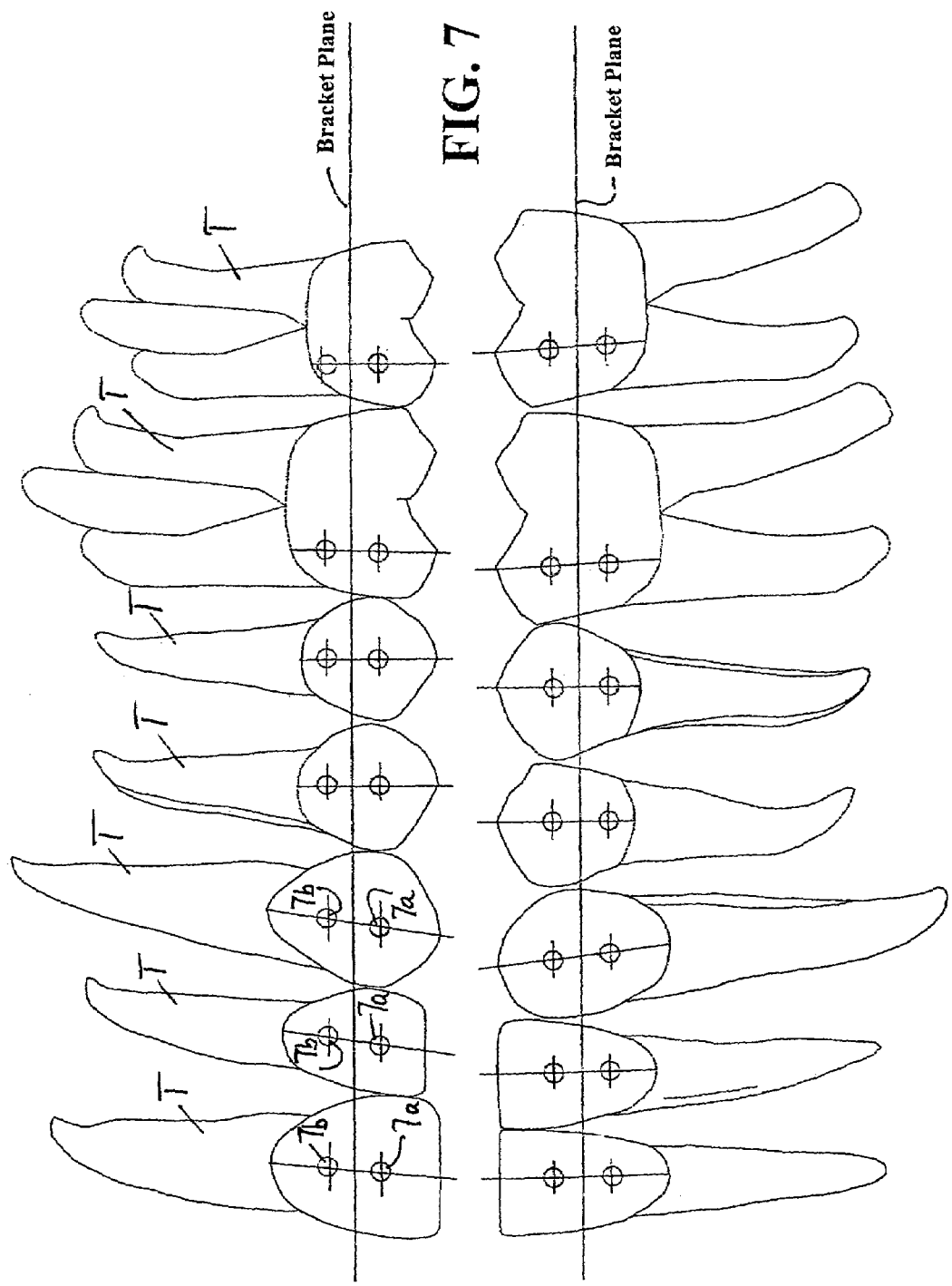

METHOD OF DETERMINING THE SELECTION OF BRACKETS WHICH ARE TO BE USED IN THE ORTHODONTIC TREATMENT OF TEETH MALPOSITION

RELATED APPLICATION

This application claims the benefit of DE 10 2004 006 009.6, filed on Feb. 6, 2004, the contents of which are incorporated herein.

FIELD OF THE INVENTION

The invention refers to a method of determining the selection of brackets for the orthodontic treatment of malposition of the human dentition.

BACKGROUND OF THE INVENTION

It is known that the masticatory apparatus is one of the most densely nervously supplied areas of the human body and is subject to a very finely regulated control. The nerve fibers in the dentinal tubes, which partially reach up to the border between the enamel and the dentine, sense any change in load within the tooth, see in this respect Ruzicka B, Stainer M, Niederwanger A and Kulmer S: "Anatomische und funktionelle Details der Schneidezähne natürlich gewachsener unbehandelter Jugendlicher und Messwerte der Seitenzähne im internationalen Vergleich", in "Stomatologie" May 1999: 96.3; pg. 45–53.

A naturally predetermined harmony exists between the parts in the stomatognathic system without which an undisturbed function would not be ensured. The musculature of the masticatory apparatus sensibly reacts to the load of the tooth, and by self-restriction (intra-dental proprioception) of the masticatory and biting forces it prevents the tooth from being damaged. Failures in the masticatory system lead to an increased activity of the masticatory muscles, which, if it lasts for a longer period of time, leads to a hypertrophy of the respective muscles and may even change the physiognomy of the face.

A balanced occlusion has the greatest muscular activity during pressing and grinding and delivers the highest mechanical loads for the entire masticatory apparatus. The mediotrusional contacts disturb mastication. Each additionally guiding tooth increases the muscular activity during pressing and grinding. A group guiding does obviously not change the interaction of the masticatory muscles during mastication, it does, however, change during pressing and grinding. In the case of a front-cuspid tooth guided occlusion and in a group guiding up to maximally the second premolar, only as much power is exerted during mastication as it is necessary for crushing the food. The occlusal concept of sequential guiding with front-cuspid tooth dominance therefore has the most favourable properties.

An orthodontic treatment of teeth malposition shall therefore not only be geared to aesthetic aspects, but must also take guiding of the teeth during mastication into consideration in order to avoid local load peaks leading to damage of the tooth. To reduce the loads in the masticatory apparatus, a proper occlusion with a front-cuspid tooth guiding is vitally important. The standard values of inclinations of the guide elements in the masticatory apparatus must, however, be individualized for any individual patient according to the skeletal proportions and functional parameters of the mandibular joints. However, practice has proven that the individual deviations from standard values in this respect are small. However, the dental anatomies are different from patient to patient, which is why the most different brackets are required if the guide surface angle (that is the angle between the guide elements or straight lines and the axis-orbital plane, AOP) is identical in case it is intended to correct teeth malpositions by means of these brackets.

A bracket usually has a slot of a rectangular cross section for accommodating an arch wire, which is pressed by a resilient ligature or spring onto the bottom of the slot. The angle (in technical language it is often referred to as "torque") defined between a plane determined by the bottom of the slot and a bottom plate of the bracket to be attached to the tooth determines the torque (thus "torque") by means of which the tooth shall be moved from a tilted malposition into a target position when using an arch wire of a rectangular or square cross section due to a positive fit between an initially twisted arch wire and the walls of the bracket slot. At the end of the treatment, this torque shall be zero, which is why the individual bracket must be chosen such that said torque angle fits to the respective tooth.

Guide elements on the teeth are such points which contact each other and slide on each other when closing the tooth rows and when moving them against each other. In the sequential guide, the guide elements successively supersede in their functions. The decrease in length and inclination of guide elements with respect to the AOP from the front over the cuspid tooth up to the premolar and molar range is characteristic for this concept, see Stainer M, Hilbe M, Leja W and Kulmer S in: "Neigung und Sequenz von Führungselementen in Gruppen geführten Okklusionen", in Dtsch Zahnärztl. Z. 1999: 54; 325–328. The AOP is a plane in which the axis of the mandibular joint and the lower edge of the left bony orbital arch are located. The functional principle of the side tooth guide is enabled by this feature of the guide elements: each side tooth discludes on the laterotrusional side all distally following teeth and all following teeth of the mediotrusional side. The lingual surfaces and edge beads of the front teeth and cuspid teeth of the maxilla as well as the mesial edge rails and buccal cusp flanks of the premolars and molars of the maxilla apply as guide elements, see the above-cited essay of Ruzicka and others, page 46, right column bottom.

Tests on a variety of patients of the most different geographical origin, whose dentitions were measured by a 3D digitizer, revealed that the measuring points and the guide elements on the teeth determined by these measuring points substantially correspond to each other.

The determination of the correct torque angle, i.e. the correct selection of the brackets, is one of the essential procedures in the course of an orthodontic treatment, which is shared by the orthodontist as the attending physician and the laboratory doing the preliminary work for the physician. The orthodontist makes an impression of the current dentition of the patient to be treated, and the laboratory determines on the basis of a cast made from the impression the brackets required for the orthodontic treatment, which the orthodontist then attaches at predetermined positions on the patient's teeth. Up to now, the palatal tooth shape was not taken into consideration, or only to a small extent, when selecting brackets to be attached at the labial side of the teeth. Success of treatment was therefore sometimes not optimal in terms of tooth guiding. The invention intends to find a remedy in this respect.

SUMMARY OF THE INVENTION

The invention starts out from the consideration that on the basis of a predetermined arrangement of guide elements uniform for all types of dentition, the tooth position is corrected such that the above-mentioned given spatial arrangement of the guide elements is achieved so that the bracket merely has to be selected for the individual tooth in consideration of a guide line or plane determined for the tooth, its angular position with respect to the bracket plane in consideration of the position of the axis-orbital plane (AOP), and the individual tooth anatomy on the labial side of the tooth. The bracket plane is the plane in which the arch wire connecting the brackets with one another is located, or, alternatively, each plane parallel thereto.

The invention is based on the object to provide a method of determining the torque angles of orthodontic brackets in consideration of the individual tooth shape and of the closing mechanism of the respective dentition.

According to the invention, a method of determining the torque angle of an orthodontic bracket for use in the treatment of teeth malpositions of a human dentition is provided, comprising the following steps:

The angle enclosed between the bracket plane and the axis-orbital plane of the dentition is determined; and for each tooth to be treated, the position of two points predetermined on the lingual side of the respective tooth are measured, if an incisor or cuspid tooth is concerned, and the position of three points predetermined on the cusps are measured, if a premolar or molar is concerned; two predetermined points defining attachment positions of brackets are measured on the labial side of the respective tooth; an individual target angle of intersection individual for the respective tooth is predetermined, said target angle being enclosed by the axis-orbital plane and a guiding straight line defined by the two predetermined points on the lingual side of each respective incisor or cuspid tooth and by a guiding plane defined by the three points on the cusps of a premolar or molar tooth, respectively; the angle of intersection of a straight line extending through said two points on the labial side of the respective tooth with the bracket plane is determined in consideration of the predetermined target angle of intersection between its guiding straight line and guide plane, respectively, and the axis-orbital plane; and the deviation of the angle of intersection of the straight line extending through said two points on the labial side of the respective tooth with the bracket plane from the vertical onto the bracket plane is determined as the torque angle of the bracket searched for the treatment of this tooth.

In an alternative embodiment of the invention, to determine the individual target angle of intersection individual for a premolar or a molar tooth, rather than a guiding plane, a guiding straight line is used which extends through two points predetermined on the cusps of such tooth, one of them being the central stop on the shoulder, being the starting point of eccentric motions, and the other being the point where the shoulder turns to the crest line of the cusp.

According to a preferred embodiment of the method, the positions of the points to be measured are determined with respect to a predetermined, three-dimensional system of coordinates that is determined by the axis-orbital plane of the patient.

According to another preferred embodiment, the positions of the points to be measured are determined with respect to a predetermined, three-dimensional system of co-ordinates, which is determined by the bracket plane of the patient.

According to a further preferred embodiment, said points are measured by means of a movable measuring head of a 3-D digitizer.

The invention leads to a correction result of a teeth malposition, in which the correction of the tooth position in the front dominantly considers the lingual flanks and in the side tooth portion it dominantly considers the buccal cusps, even if this is at the expense of ideal looks on the labial side, since a healthy function of the dentition due to a proper tooth guide when biting and chewing is usually more important to the patient than perfect looks of the rows of teeth on the labial side.

The invention first of all provides a measuring of the entire dentition of the patient in a manner known per se for determining the target position of the guide elements, which shall be achieved by the correction of the teeth malposition. It supplements this measurement by a measurement of the tooth anatomy also on the labial side of the dentition and by a calculation of the torque angles of all brackets to be used in the orthodontic treatment of the respective patient by taking all measured values into consideration.

The invention will now be described with reference to the drawings.

BRIEF DESCRIPTION OF THE DRAWINGS

FIG. 2 shows a section of an incisor of the maxilla and mandible to explain the guide function.

FIG. 3 shows the view of a row of teeth of a maxilla in top plan view onto the bracket plane.

FIG. 7 shows the one half of rows of teeth of the maxilla and mandible seen from the labial side to explain adhesive points of brackets.

DETAILED DESCRIPTION OF PREFERRED EMBODIMENTS

Figure 1:
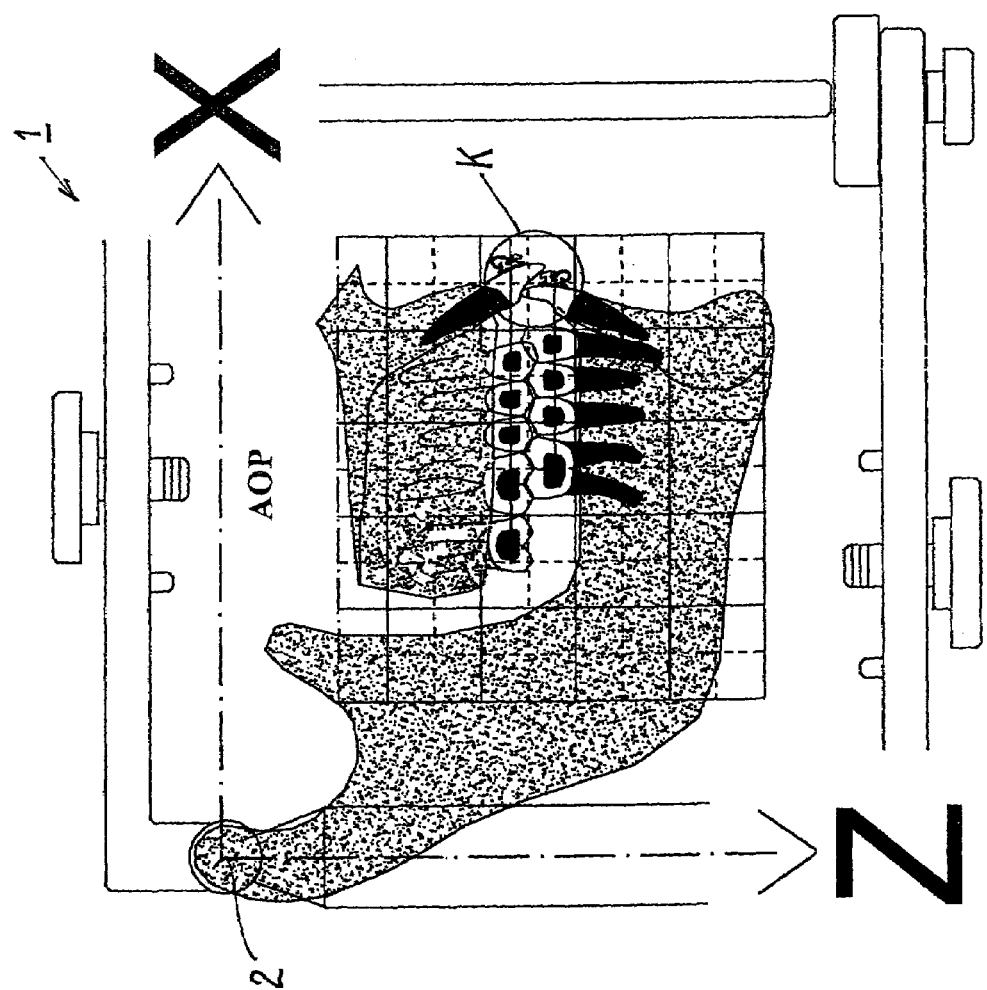
FIG. 1 shows a diagrammatic partial view of a model of the human dentition in an articulator, seen in the axial direction thereof.

FIG. 1 shows as a partial view from a side partially cut the model of the human dentition in an articulator 1, with frame elements and particularly the model of a mandibular joint 2. The mandibular joint 2 defines a mandibular joint axis (direction Y, not shown) extending perpendicularly to the drawing plane. The mandibular joint axis serves amongst others for the positional definition of a plane, which extends through the mandibular joint axis and the lower edge of the left bony orbital arch. This plane is the already mentioned axis-orbital plane AOP. It is for instance used to determine, together with a vertical onto said plane, a three-dimensional system of coordinates to measure the dentition. This will be explained later on.

FIG. 1 further shows the model of a mandible and partially a maxilla with the associated rows of teeth. The detail in the front tooth area is emphasized by a circle K.

Contrary to the purely pivoting movement of the mandible with respect to the maxilla in an articulator according to FIG. 1, the human mandible is not only pivotal with respect to the maxilla in the dentition but it is also movable in the direction towards the mandibular joint axis and transversely thereto in order to be able to cause grinding movements. This mutual adjustment of the jaws results in the fact that during the closing movement of the dentition the teeth are not compulsorily set onto each other, as is the case in chattering of teeth, but they can also slide past each other which causes amongst others the already mentioned grinding movements. This is shown with the example of the detail K of FIG. 1 in FIG. 2 for two front teeth. As can be seen in the partial drawing (a), the front teeth participating in the closing movement can be opposed to one another with their cutting edges, and during the further closing process, the incisor of the mandible slides along the lingual side of the front tooth of the maxilla, as shown in partial drawing (b), to finally reach the end position shown in partial drawing (c), as also shown in FIG. 1. Thus, the teeth guide each other during the closing movement. As mentioned above, the selection of the brackets used for a correction of teeth malposition shall particularly take this guide function into consideration.

The guide elements, these are straight lines in the front tooth and cuspid tooth area, and these are planes in the premolar and molar area, must be determined according to their position to be able to determine with their help the torque angle of the bracket in consideration of the tooth anatomy and the angle between the axis-orbital plane AOP and the bracket plane. FIG. 3 shows measuring points $3a$ and $3b$ on incisors and cuspid teeth defined for this purpose as well as $4a$, $4b$ and $4c$ on premolars and molars. The position of the above-mentioned measuring points is predetermined by developed systems, for which reference is made to the above-mentioned essay from "Stomatologie", where further sources are cited.

According to the aforementioned article in "Stomatologie", at an incisor or a cuspid tooth, the first predetermined measuring point $3a$ the position of which is to be determined is defined as follows. If a tangent line is drawn from an apex where the rear surface of an incisor or cuspid tooth transits from a convex shape to a concave shape in incisal direction to a most prominent point at the lingual surface of said tooth, the point is attained where the lingual rear surface of the tooth joins the incisal edge of the tooth. This point is defined as the first predetermined point $3a$. The second predetermined point $3b$ of the tooth is the point where the incisal edge of the lower jaw's tooth confronting said upper jaw's tooth actually contacts same upon closing the dentition.

As to the premolars and molars, according to the aforementioned article in "Stomatologie", the points of interest the positions of which are to be determined are defined as follows. At a premolar, the first point $4a$ is the apex of the buccal cusp. At a molar, the first point $4a$ is the apex of the mesio-buccal cusp. At premolars as well as at molars, the second point $4b$ is the turning point between the shoulder and the crest line of the cusp, and the third point $4c$ is the central stop on the shoulder and is the starting point of eccentric motions.

The position of these measuring points in a for instance three-dimensional system of coordinates is determined, which may for instance be implemented by a 3-D digitizer. The measuring accuracies of such digitizers are in a scale of 0.05 mm.

Figure 5:
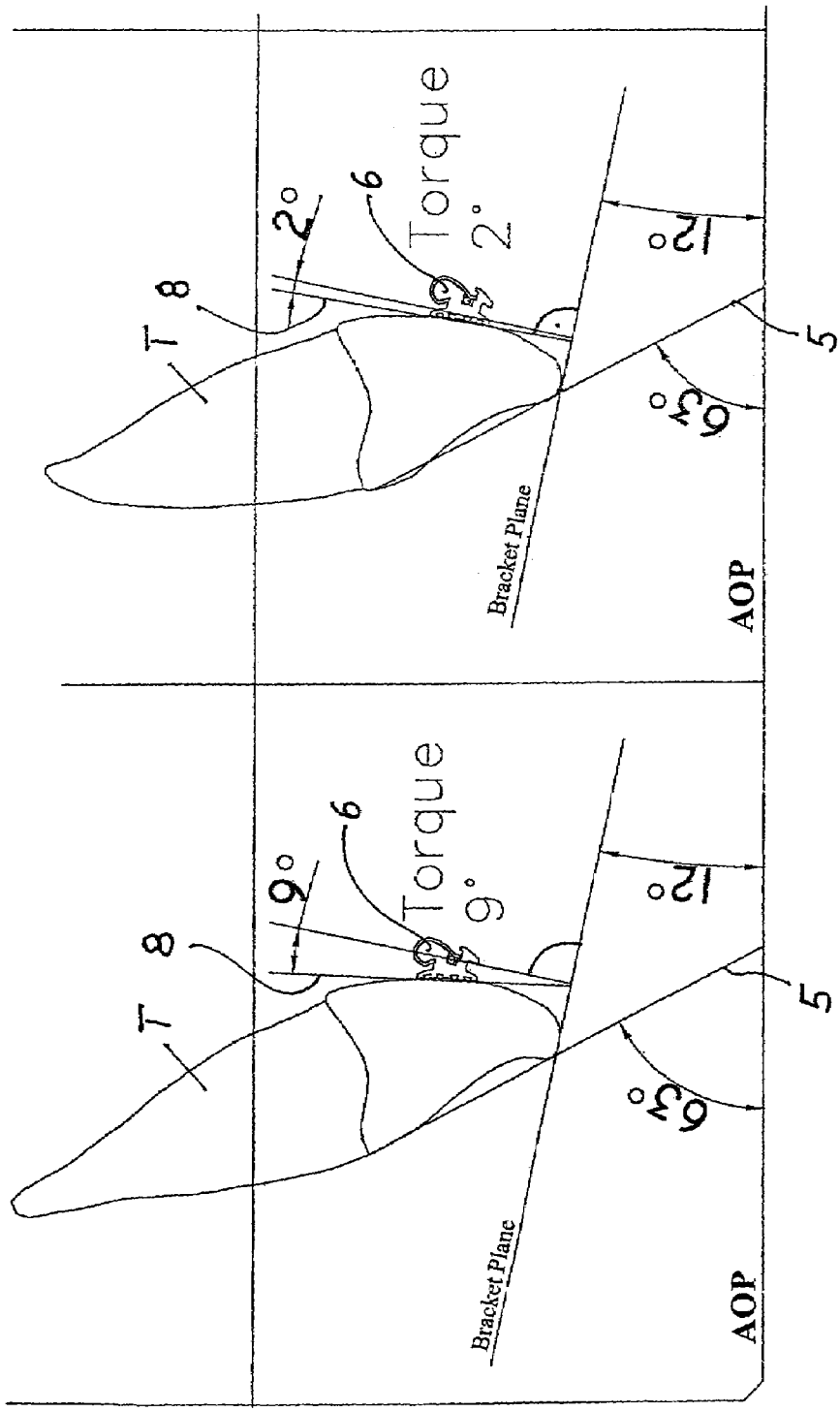
FIG. 5 shows a section of FIG. 4 in an enlarged scale.
Figure 6:
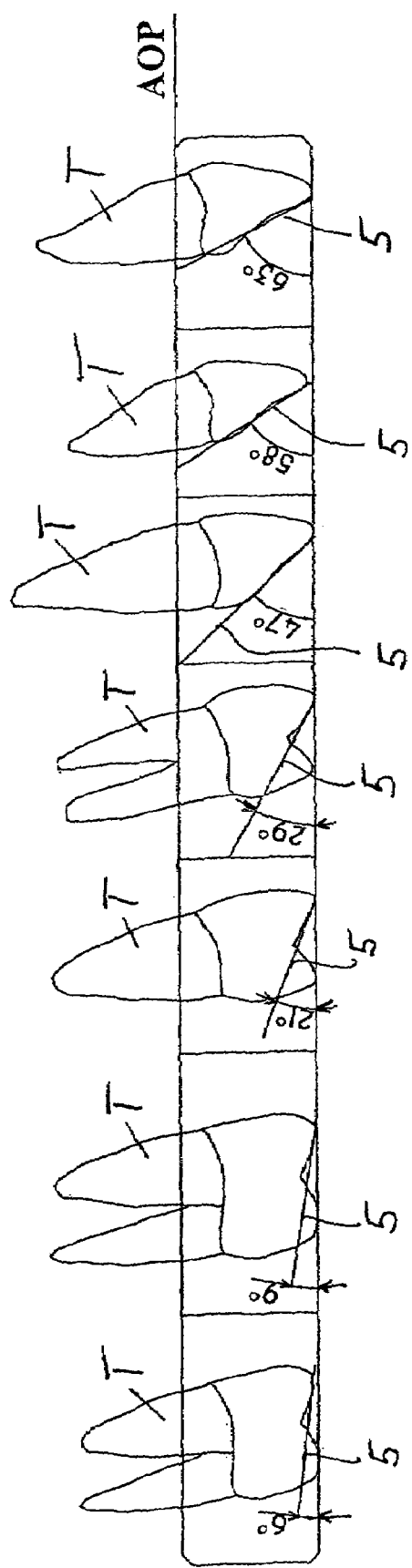
FIG. 6 shows the one half of a row of teeth with a view of a guide elements inclined differently depending on the tooth.

By means of the measuring points $3a$ and $3b$, and $4a$ to $4c$, respectively, determined in this manner in the three-dimensional system of coordinates, guide lines or guide planes can be calculated. Guide lines of this kind are characterised with reference numeral 5 in the example of incisors shown in FIG. 4 and FIG. 5. This guide line 5 intersects the axis-orbital plane AOP at a predetermined angle. It has proven from a plurality of measurements on dentitions of the most different persons that this angle shall be for example 63° for the middle front teeth. Other angles apply for other teeth. According to FIG. 6, the angle shall be 58° for the second front teeth and 47° for the cuspid teeth. A guide plane 5 is defined for the premolars and molars, which cuts the axis-orbital plane AOP at an angle, which according to FIG. 6 is 29° and 21°, respectively, for the premolars, and 9° and 6°, respectively, for the molars.

Alternatively, instead of using a guide plane defined by three points on the premolars and molars, respectively, a guiding straight line defined by two points referenced by $4b$ and $4c$ in FIG. 3 may be used to define a predetermined angle of intersection of the aforementioned kind.

Figure 4:
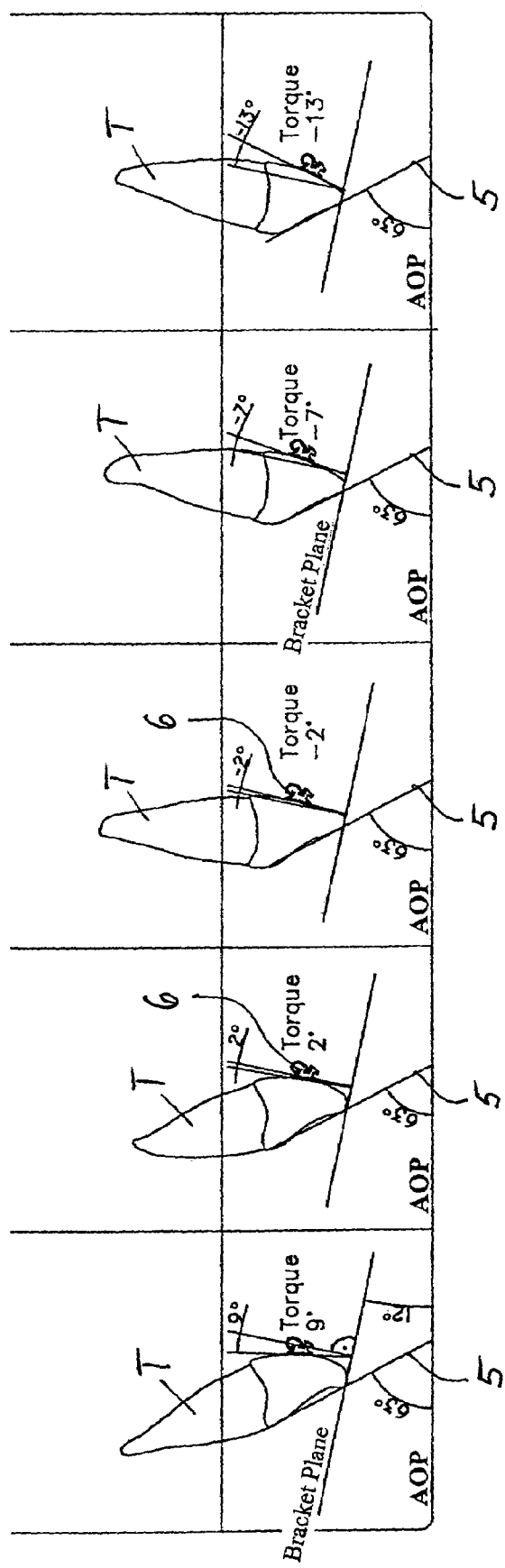
FIG. 4 shows different tooth shapes to elucidate the different bracket selection.

FIG. 4 shows several middle front teeth T of different anatomy, which require the use of different brackets, although the angle of intersection between the guiding straight line 5 and the axis-orbital plane AOP is equal and the angle of intersection between the bracket plane and the axis-orbital plane AOP is 12° in all cases. For a better clarity, reference is made in this respect to FIG. 5 regarding the two examples shown on the left hand side.

To determine the torque angle that the bracket 6 to be attached on the respective tooth shall have, the labial side of the tooth T must be measured. For this purpose, according to FIG. 7, two measuring points $7a$ and $7b$ are defined on the labial side of each tooth, which determine the position of the bracket that is to be attached onto the respective tooth. The points $7a$ and $7b$ are located underneath the occlusal and gingival edges of the base plates of the brackets that are cemented onto the teeth. Usually, these base plates have a distance of 3 mm to the tooth edge, i.e. from its cutting edge, except for the second incisor of the maxilla, whose cutting edges are usually slightly offset compared to the other teeth. Depending on the bracket type used, the second point $7b$ has a distance from the first point $7a$, which is for instance 3.5 mm. If a line is drawn in the centre between the individual teeth, the bracket plane results.

If the inclination of the bracket plane with respect to the axis-orbital plane AOP has been determined, and further the angle of intersection between the guiding straight line or guiding plane 5 with the axis-orbital plane AOP has been determined and points $7a$ and $7b$ have been measured, the position of a line 8 determined by points $7a$ and $7b$ (see FIG. 5), which is representative for the tooth front, can be determined with respect to the bracket plane. The angle between this line 8 and a vertical on the bracket plane defines, according to FIG. 5, the torque angle that the bracket 6 must have that shall be attached onto the respective tooth T.

The above-mentioned measuring procedures and calculations that use the measured values and angular definitions, can be carried out in the laboratory without the intervention of a physician being required. The orthodontist only intervenes after the selection of the brackets to be used was made.

While the principles of the invention have been shown and described in connection with specific embodiments, it is to be understood that such embodiments are by way of example and are not limiting.

The invention claimed is:

1. A method of determining a torque angle of an orthodontic bracket for use in a treatment of teeth malposition of a human dentition, the method comprising the following steps:
   a) determining an angle enclosed between a bracket plane and an axis-orbital plane of a dentition, and
   for each tooth to be treated b) measuring positions of two predetermined points on a lingual side of an incisor and of a cuspid tooth, and three predetermined points on cusps of a premolar and molar, respectively, c) measuring positions of two further predetermined points defining attachment positions of a bracket on a labial side of the respective tooth, d) predetermining an individual target angle of intersection between the axis-orbital plane and one of a guiding straight line defined by said two predetermined points of an incisor or a cuspid tooth and a guiding plane defined by said predetermined points of a premolar and molar, respectively, e) determining the angle of intersection of a straight line extending through said further two points on the labial side of the respective tooth with the bracket plane in consideration of said predetermined target angle of intersection between the axis-orbital plane and said guiding straight line and guiding plane, respectively, and f) determining a deviation of an angle of intersection of said straight line extending through said further two points on the labial side of the respective tooth with the bracket plane from a vertical onto the bracket plane, wherein this deviation represents the torque angle.

2. A method as claimed in claim 1, wherein said points are measured by means of a movable measuring head of a 3-D digitizer.

3. A method as claimed in claim 1, wherein the positions of the points to be measured are determined with respect to a predetermined, three-dimensional system of coordinates that is determined by the axis-orbital plane of the patient.

4. A method as claimed in claim 3, wherein said points are measured by means of a movable measuring head of a 3-D digitizer.

5. A method as claimed in claim 1, wherein the positions of the points to be measured are determined with respect to a predetermined, three-dimensional system of coordinates, which is determined by the bracket plane of the patient.

6. A method as claimed in claim 5, wherein said points are measured by means of a movable measuring head of a 3-D digitizer.

7. A method of determining a torque angle of an orthodontic bracket for use in a treatment of teeth malposition of a human dentition, the method comprising the following steps:

a) determining an angle enclosed between a bracket plane and an axis-orbital plane of a dentition, and for each tooth to be treated b) measuring positions of two predetermined points on a lingual side of an incisor and of a cuspid tooth, and on cusps of a premolar and molar, respectively, c) measuring positions of two further predetermined points defining attachment positions of a bracket on a labial side of the respective tooth, d) predetermining an individual target angle of intersection between the axis-orbital plane and a guiding straight line defined by said two predetermined points, e) determining the angle of intersection of a straight line extending through said further two points on the labial side of the respective tooth with the bracket plane in consideration of said predetermined target angle of intersection between the axis-orbital plane and said guiding straight line, and f) determining a deviation of an angle of intersection of said straight line extending through said further two points on the labial side of the respective tooth with the bracket plane from a vertical onto the bracket plane, wherein this deviation represents the torque angle.

8. A method as claimed in claim 7, wherein said points are measured by means of a movable measuring head of a 3-D digitizer.

9. A method as claimed in claim 7, wherein the positions of the points to be measured are determined with respect to a predetermined, three-dimensional system of coordinates that is determined by the axis-orbital plane of the patient.

10. A method as claimed in claim 9, wherein said points are measured by means of a movable measuring head of a 3-D digitizer.

11. A method as claimed in claim 7, wherein the positions of the points to be measured are determined with respect to a predetermined, three-dimensional system of coordinates, which is determined by the bracket plane of the patient.

12. A method as claimed in claim 11, wherein said points are measured by means of a movable measuring head of a 3-D digitizer.

* * * * *